US00PP12802P2

(12) United States Plant Patent
Meilland

(10) Patent No.: US PP12,802 P2
(45) Date of Patent: Jul. 23, 2002

(54) FLORIBUNDA ROSE PLANT NAMED 'MEISPONGE'

(75) Inventor: Alain A. Meilland, Antibes (FR)

(73) Assignee: CP (Delaware), Inc., Wilmington, DE (US)

( * ) Notice: Subject to any disclaimer, the term of this patent is extended or adjusted under 35 U.S.C. 154(b) by 0 days.

(21) Appl. No.: 09/697,167

(22) Filed: Oct. 27, 2000

(51) Int. Cl.[7] ..... A01H 5/00
(52) U.S. Cl. ..... Plt./143
(58) Field of Search ..... Plt./143, 142, 141

(56) References Cited

PUBLICATIONS

Protection Des Obtentions Vegetales, Bulletin Officiel du Comité de la Protection des Obtentions Végétales, Cover Page and pp. 124, 132, 136 and 142 (Apr. 10, 1999).

Protection Des Obtentions Vegetales, Bulletin Officiel du Comité de la Protection des Obtentions Végétales, Cover Page and pp. 288 and 293 (Jul. 10, 1999).

UPOV–ROM GTITM Computer Database 2001/03, Jun. 21, 2001, GTI Jouve Retrieval Software, Citation for Rosa 'Meisponge'.*

* cited by examiner

*Primary Examiner*—Bruce R. Campell
*Assistant Examiner*—June Hwu
(74) *Attorney, Agent, or Firm*—Burns, Doane, Swecker & Mathis, L.L.P.

(57) ABSTRACT

A new and distinct variety of Floribunda rose plant is provided which forms attractive large bicolored blossoms that are relatively stable in coloration. Such blossoms possess no fragrance. The blossoming is particularly attractive in the spring. The plant exhibits a compact, generally uniform and bushy growth habit, forms dense medium green and dull foliage, and possesses very good disease resistance. The new variety is particularly well suited for providing colorful ornamentation in the landscape.

1 Drawing Sheet

SUMMARY OF THE INVENTION

Figures 1, 2, 3, 4, 5, 6, 7, 8, 9, 10, 11, 12, 13, 14, 15, 16:
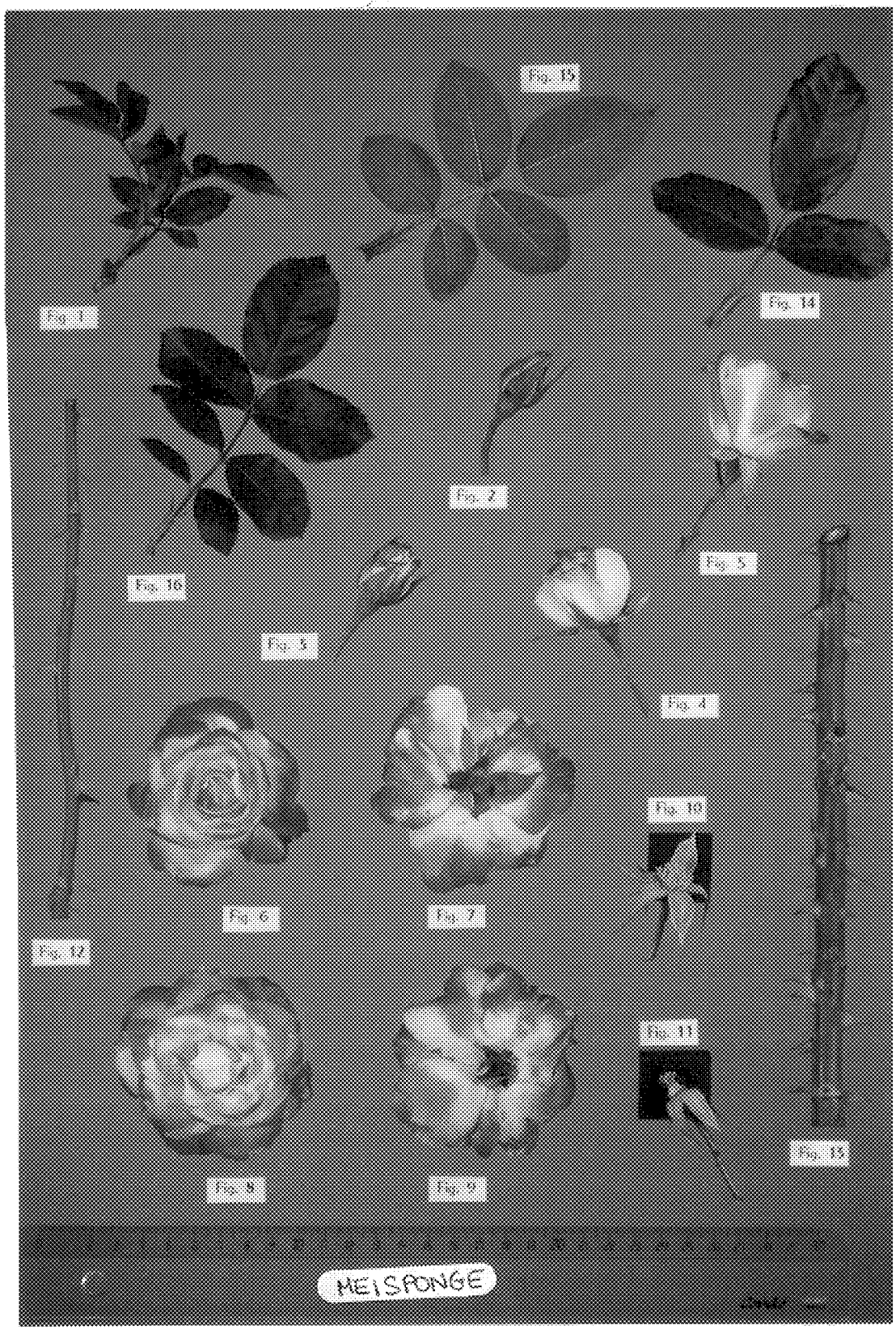

The new Floribunda variety of *Rosa hybrida* of the present invention was created by artificial pollination wherein two parents were crossed which previously had been studied in the hope that they would contribute the desired characteristics. The female parent (i.e., the seed parent) of the new variety was the 'Meichoiju' variety (non-patented in the United States). The male parent (i.e., the pollen parent) was the product of the cross of the 'Meidanu' variety (non-patented in the United States) and the 'Macman' variety (non-patented in the United States). The 'Macman' variety sometimes is known as the 'Matangi' variety. The parentage of the new variety can be summarized as follows:

'Meichoiju'×('Meidanu'×'Macman').

The seeds resulting from the above pollination were sown and small plants were obtained which were physically and biologically different from each other. Selective study resulted in the identification of a single plant of the new variety.

It was found that the new variety of Floribunda rose plant of the present invention possesses the following combination of characteristics:

(a) forms attractive large bicolored white and red blossoms that are relatively stable in coloration, (b) exhibits a compact, generally uniform and bushy growth habit, (c) forms attractive dense medium green dull foliage, and (d) is particularly well suited for growing as ornamentation in parks and gardens.

The new variety well meets the needs of the horticultural industry and is particularly well suited for growing in the landscape.

The new variety of the present invention can be readily distinguished from its parental varieties. For instance, the 'Meichoiju' variety forms pink blossoms of a uniform coloration, the 'Meidanu' variety forms red blossoms with a slight fragrance and uniform coloration, and the 'Macman' variety forms dissimilar ovoid-shaped buds.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meisponge' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were one year of age and were observed during June while budded on *Rosa froebelli* understock and growing outdoors at Le Cannet des Maures, Var, France. Dimensions in centimeters are indicated at the bottom of the photograph.

FIG. 1 — illustrates a specimen of a young shoot;

FIG. 2 — illustrates a specimen of a floral bud before the opening of the sepals;

FIG. 3 — illustrates a specimen of a floral bud at the opening of the sepals;

FIG. 4 — illustrates a specimen of a floral bud at the opening of the petals;

FIG. 5 — illustrates a specimen of a flower in the course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates a specimen of a leaf with three leaflets — plan view — upper surface;

FIG. 15 — illustrates a specimen of a leaf with five leaflets — plan view — under surface; and FIG. 16 — illustrates a leaf with seven leaflets — plan view — upper surface.

DETAILED DESCRIPTION

The chart used in the identification of the colors is that of The Royal Horticultural Society (R.H.S. Colour Chart). The description is based on the observation of one year-old plants during October while budded on *Rosa froebelli* understock and growing outdoors at Le Cannet des Maures, Var, France. The coloration in common terms precedes reference to the chart in some instances.

Class: Floribunda.

Plant:

*Height.*—Approximately 70 to 80 cm on average at the end of the growing season.

*Width.*—Approximately 80 cm on average at the end of the growing season.

*Habit.*—Bushy.

Branches:

*Color.*—Young stems: near Yellow-Green Group 146B and 146C. Adult wood: near Yellow-Green Group 146A and 146B.

*Thorns.*—Size: approximately 1.5 cm in length on average. Quantity: moderately numerous (as illustrated). Color: near Greyed-Orange Group 163A and 163B on young stems and near Greyed-Orange Group 167A and 167B on adult wood. Shape: slightly concave.

Leaves:

*Stipules.*—Adnate, pectinate, Yellow-Green Group 146A in coloration, approximately 2 cm in length on average, and approximately 0.7 cm in width on average.

*Petioles.*—Upper surface: non-glandular and with some anthocyanin coloration when young. Under surface: commonly with a few prickles and with some anthocyanin coloration when young.

*Leaflets.*—Number: 3, 5, and 7 (most often). Shape: generally elliptic with a cuspidate tip and an obtuse base. Serration: regular (as illustrated). Texture: thick and smooth on both surfaces. General appearance: very dense, medium green, and dull foliage. Color (young foliage): Upper surface: near Green Group 139A with some anthocyanin coloration of Greyed-Purple Group 183A. Under surface: near Yellow-Green Group 146A with some anthocyanin coloration of Greyed-Purple Group 183A. Color (adult foliage): Upper surface: near Green Group 139A. Under surface: near Yellow-Green Group 146A.

Inflorescence:

*Number of flowers.*—Usually 2 to 5 flowers per stem.

*Peduncle.*—Long, commonly approximately 5.5 cm in length on average, rigid, smooth, and near Yellow-Green Group 144A, and sometimes some anthocyanin coloration of Greyed-Purple Group 183A.

*Sepals.*—Upper surface: tomentose, and near Yellow-Green Group 146C and 146D in coloration. Under surface: smooth and near Yellow-Green Group 144A with anthocyanin coloration of near Greyed-Purple Group 183A. Size: approximately 2.5 cm in length on average. Configuration: commonly with a few weak extensions.

*Buds.*—Shape: conical. Size: medium. Length: approximately 2 cm on average. Color upon opening: Upper surface: near white Group 155D and widely suffused with Red Group 47A. Under surface: near White Group 155D and widely suffused with Red Group 47A.

*Flower.*—Shape: flat cup-shaped. Diameter: commonly approximately 8 to 10 cm on average. Color (when opening begins): Upper surface: near White Group 155D and widely suffused with Red Group 47A. Under surface: near White Group 155D and widely suffused with Red Group 47A. Color (when blooming): Upper surface: near White Group 155D and widely suffused with Red Group 47A. Under surface: near White Group 155D and widely suffused with Red Group 47A. Color (at end of opening): Upper surface: near White Group 155D and widely suffused with Red Group 47A. Under surface: near White Group 155D and widely suffused with Red Group 47A. Fragrance: none. Lasting quality: long and commonly approximately 10 days on average on the plant. Petal shape: wedge-shaped base and a reflexed tip. Petal number: commonly approximately 35 on average. Petal size: commonly approximately 3.5 cm in length on average and approximately 3.2 cm in width on average. Petal texture: relatively thick and rigid. Petal drop: good, the petals commonly detach cleanly. Petaloids: none observed. Stamen number: approximately 52 on average. Anthers: approximately 0.2 cm in size and near Yellow-Orange Group 16A in coloration. Filaments: approximately 0.6 cm in length on average and near Green-Yellow Group 1B in coloration. Pollen: present and yellow in coloration. Pistil number: approximately 45 on average. Stigmas: near Yellow Group 11A in coloration. Styles: approximately 0.4 cm in length on average and near Green-Yellow Group 1C in coloration. Receptacle: near Yellow-Green Group 144A in coloration, and in longitudinal section in the shape of a funnel. Hips: near Greyed-Orange Group 171B in coloration. Seeds: elongated, approximately 0.3 cm in length and near white in coloration.

Development:

*Blooming.*—Particularly attractive during the spring.

*Resistance to diseases.*—Very good with respect to Powdery Mildew and Black Spot.

*Aptitude to bear fruit.*—Good.

*Hardiness.*—Has withstood temperatures above −10° C.

I claim:

1. A new and distinct variety of Floribunda rose plant characterized by the following combination of characteristics:

(a) forms attractive large bicolored white and red blossoms that are relatively stable in coloration, (b) exhibits a compact, generally uniform and bushy growth habit, (c) forms attractive dense medium green dull foliage, and (d) is particularly well suited for growing in parks and gardens;

substantially as herein shown and described.

* * * * *

MEISPONGE